United States Patent [19]

Komoto et al.

[11] Patent Number: 5,063,222

[45] Date of Patent: Nov. 5, 1991

[54] ANTIINFLAMMATORY DEXAMETHASONE 17α-CYCLOPROPANECARBOXYLATES WITH REDUCED SYSTEMIC ACTIVITY

[75] Inventors: Teruo Komoto, Chiba; Junji Okawa, Narita; Yoichiro Ogawa, Chiba; Susumu Sato, Shisui; Naokata Taido, Funabashi; Tadayuki Kuraishi, Chiba, all of Japan

[73] Assignee: SS Pharmaceutical Co., Ltd., Tokyo, Japan

[21] Appl. No.: 508,686

[22] Filed: Apr. 13, 1990

[30] Foreign Application Priority Data

Apr. 19, 1989 [JP] Japan .................................. 1-99762

[51] Int. Cl.$^5$ .......................................... A61K 31/56
[52] U.S. Cl. .................................... 514/180; 552/574; 552/581
[58] Field of Search ................. 514/180; 552/574, 581

[56] References Cited

U.S. PATENT DOCUMENTS 3,992,422 11/1976 Green .................................. 552/581
4,021,459 5/1977 Green .................................. 552/581

FOREIGN PATENT DOCUMENTS 2853785 6/1980 Fed. Rep. of Germany ...... 552/581

Primary Examiner—Mukund J. Shah
Assistant Examiner—Matthew V. Grumbling
Attorney, Agent, or Firm—Oblon, Spivak, McClelland, Maier & Neustadt

[57] ABSTRACT

Steroid derivatives represented by formula (I) are disclosed.

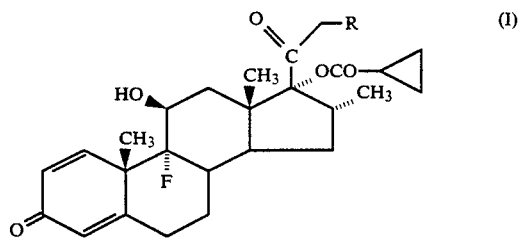

wherein R is a hydrogen atom, a halogen atom, a hydroxy group, or a group —OCOR$_1$, wherein R$_1$ is a linear or branched alkyl group which may be substituted by a halogen atom or a cycloalkyl group, a cycloalkyl group, or an aryl group. The compounds are useful for curing or alleviating inflammation or rheumatism.

2 Claims, No Drawings

ANTIINFLAMMATORY DEXAMETHASONE 17α-CYCLOPROPANECARBOXYLATES WITH REDUCED SYSTEMIC ACTIVITY

BACKGROUND OF THE INVENTION

1. Field of the Invention

This invention relates to novel steroid derivatives, processes for preparing such steroid derivatives, and pharmaceutical compositions for curing or alleviating inflammation or rheumatism comprising the same as an active component.

2. Description of the Background Arts

Many steroid derivatives are known to possess anti-inflammatory activity. They are used for the most part as drugs for external application for the treatment of chronic rheumatism and dermatosis. In recent years, steroid derivatives possessing stronger local anti-inflammatory activity, such as dexamethasone valerate, dexamethasone dipropionate, clobetasol propionate, and the like, have been developed.

These steroid derivatives, however, exert, through percutaneous absorption, systemic action along with the strong local anti-inflammatory activity. Furthermore, there is concern about side effects which may be caused by such systemic action.

Development of steroid derivatives having strong anti-inflammatory action with a high local selectivity and no side effects have therefore been desired.

In view of this situation, the present inventors have synthesized a number of ester derivatives of dexamethasone in which the 17- or 21-position —OH is esterified, and have investigated their pharmaceutical effects. As a result, the inventors have found that steroid derivatives of formula (I) below exhibited strong local anti-inflammatory action with the least systemic action, and were useful for the treatment not only of inflammation but also of rheumatism. Such a finding has led to the completion of the present invention.

SUMMARY OF THE INVENTION

Accordingly, an object of this invention is to provide a steroid derivative represented by formula (I),

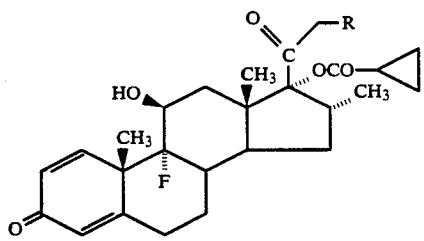

wherein R is a hydrogen atom, a halogen atom, a hydroxy group, or a group —OCOR$_1$, wherein R$_1$ is a linear or branched alkyl group which may be substituted by a halogen atom or a cycloalkyl group, a cycloalkyl group, or an aryl group.

Another object of the present invention is to provide processes for preparing steroid derivatives of formula (I).

Still another object is to provide a pharmaceutical composition for curing or alleviating inflammation or rheumatism comprising a steroid derivative as an active component.

Other objects, features and advantages of the invention will hereinafter become more readily apparent from the following description.

DETAILED DESCRIPTION OF THE INVENTION AND PREFERRED EMBODIMENTS

Fluorine, chlorine, bromine, and iodine are given as preferable halogen atoms represented by R in formula (I). Especially preferable halogen atoms are chlorine and bromine.

Preferable linear or branched alkyl groups represented by R$_1$ are those having 1-23, particularly 1-15, carbon atoms. Fluorine, chlorine, bromine, and iodine are given as preferable halogen atoms which may be substituted with the alkyl group. Especially preferable halogen atoms are chlorine and bromine. Cycloalkyl groups represented by R$_1$ are those having 3-6 carbon atoms.

Specific examples of groups represented by R$_1$ include: as linear alkyl groups, methyl, ethyl, n-propyl, n-butyl, n-nonyl, n-undecanyl, n-tridecanyl, n-pentadecanyl, and the like; as branched alkyl groups, i-propyl, i-butyl, secbutyl, t-butyl, i-pentyl, neopentyl, t-pentyl, i-hexyl, and the like; as halogenoalkyl groups, 3-chloropropyl, 3-bromopropyl, 3-fluoropropyl, 4-chlorobutyl, 4-bromobutyl, 4-fluorobutyl, 5-chloropentyl, 5-bromopentyl, 5-fluoropentyl, 6-chlorohexyl, 6-bromohexyl, 6-fluorohexyl, and the like; as cycloalkylalkyl groups, 2-cyclohexylethyl, 2-cyclopropylethyl, 2-cyclopentylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 5-cyclopropylpentyl, 5-cyclopentylpentyl, 5-cyclohexylpentyl, 6-cyclopentylhexyl, and the like; as cycloalkyl groups, cyclopropyl, cyclobutyl, cyclopentyl, cyclohexyl, and the like; and as aryl groups, phenyl, naphtyl, 2-methylphenyl, 4-methylphenyl, 2-ethylphenyl, 4-ethylphenyl, 2-methoxyphenyl, 4-methoxyphenyl, 2-ethoxyphenyl, 4-ethoxyphenyl, 2-aminophenyl, 4-aminophenyl, 4-dimethylaminophenyl, 2-hydroxyphenyl, 4-hydroxyphenyl, 2-nitrophenyl, 4-nitrophenyl, 2-chlorophenyl, 4-chlorophenyl, 2-bromophenyl, 4-bromophenyl, 2-fluorophenyl, 4-fluorophenyl, 2,6-dichlorophenyl, 2,6-dibromophenyl, biphenyl, and the like.

Compounds of formula (I) of the present invention can be prepared by known esterification, desoxydation, or halogenation. Some examples of the processes for preparing compounds of formula (I) are given below.

(1) Process for preparing a compound having a hydroxy group for R in formula (I): the compound of formula (Ia)

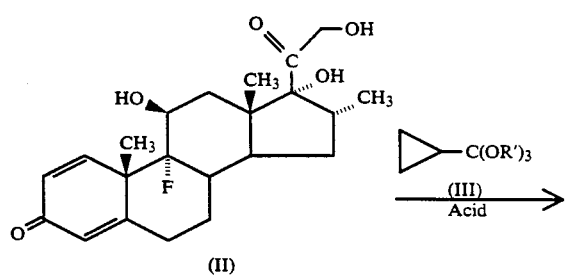

-continued

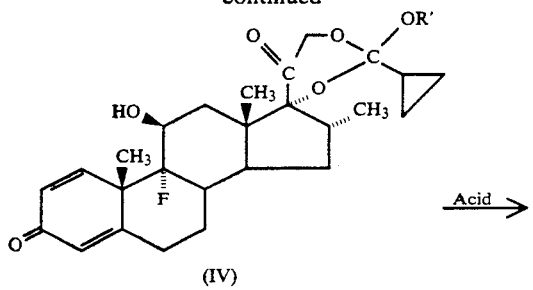

(IV)

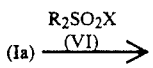

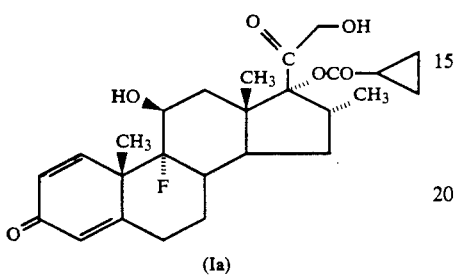

(Ia)

wherein R' represents an alkyl group.

In this process, dexamethasone (II) is reacted with a trialkyl orthocyclopropane carboxylate of formula (III) in the presence of an acid, thus producing an intramolecular orthoester compound of formula (IV). The compound of formula (IV) is then hydrolyzed to produce 17-ester compound (Ia).

Trimethyl orthocyclopropane carboxylate, triethyl orthocyclopropane carboxylate, and the like are given as examples of preferable trialkyl orthocyclopropane carboxylates of formula (III). Preferable acids which can be used in the reaction are, for example, p-toluenesulfonic acid, methanesulfonic acid, and the like.

Hydrolysis is carried out in the presence of hydrochloric acid, acetic acid, or oxalic acid at a temperature from $-10°$ C. to room temperature.

(2) Process for preparing a compound having a group —OCOR$_1$ for R in formula (I): the compound of formula (Ib)

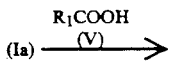

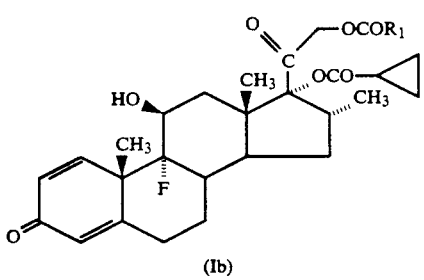

(Ib)

According to the above reaction scheme, compound (Ia) and a carboxylic acid (V) or its reactive derivatives are reacted to produce 17,21-diester derivative (Ib).

As reactive derivatives of carboxylic acid (V) which can be used in this process acid halogenides, acid anhydrides, mixed acid anhydrides, and the like are given. The reaction is preferably carried out in the presence of a tertiary amine such as pyridine, trimethylamine, triethylamine, or the like, and a deacidifying agent such as an alkali carbonate, alkali hydroxide, alkali hydride, or the like, and in a solvent which is not involved in the reaction, such as ether, tetrahydrofuran, toluene, chloroform, dichloromethane, or the like.

(3) Process for preparing a compound having hydrogen for R in formula (I): the compound of formula (Ic)

$$(Ia) \xrightarrow{R_2SO_2X \ (VI)}$$

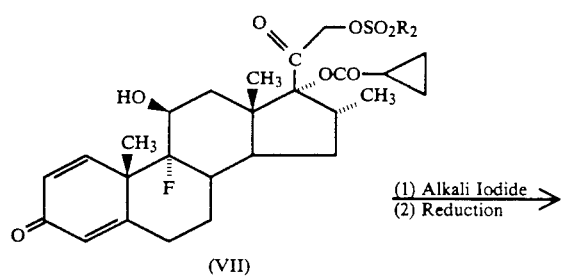

(VII)

(1) Alkali Iodide
(2) Reduction (Ic)

wherein X is a halogen atom and R$_2$ is an alkyl group or a phenyl group which may be substituted by an alkyl group.

According to the above reaction scheme, compound (Ia) is reacted with a sulfonyl halide derivative (VI) to produce 21-sulfonate derivative (VII), which is reacted with an alkali iodide followed by reduction to produce 21-desoxy derivative (Ic).

Methansulfonic acid chloride, benzenesulfonic acid chloride, toluenesulfonic acid chloride, and the like are given as examples of sulfonyl halide derivative (VI) used in the sulfonylation of the above process. The reaction is preferably carried out in the presence of a tertiary amine such as pyridine, trimethylamine, triethylamine, or the like. Sodium iodide, potassium iodide, or the like can be used for iodidation of the sulfonate derivative (VII). Reducing agents which can be preferably used in the reduction are sodium thiosulfate, sodium bisulfite, sodium methabisulfite, and the like. It is desirable that the reaction be carried out in a solvent which is not involved in the reaction, such as ether, tetrahydrofuran, toluene, chloroform, dichloromethane, or the like.

(4) Process for preparing a compound having a halogen atom for R in formula (I): the compound of formula (Id)

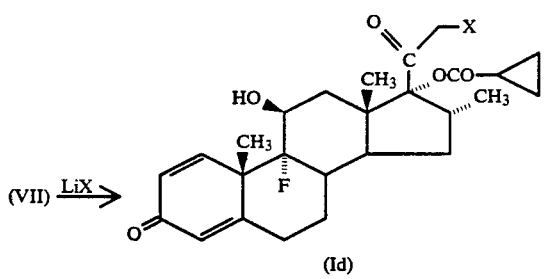

21-Halo derivative (Id) can be obtained by reacting 21-sulfonate derivative (VII) and a lithium halide.

Lithium chloride, lithium bromide, and the like are given as lithium halides used in the above process. The reaction is carried out in a solvent such as dimethylformamide or the like at a temperature of 100°–120° C. for 5–10 hours with stirring.

Other features of the invention will become apparent in the course of the following description of the experimental examples showing the anti-inflammatory effect by the use of the compounds of the present invention and the examples for the preparation thereof, which are given for illustration of the invention and are not intended to be limiting thereof.

EXAMPLES

EXPERIMENTAL EXAMPLE 1

Anti-inflammatory Effect

Using Wister male rats weighting 130–150 g, each group consisting of 6 rats, the local selectivity of the anti-inflammatory action was investigated by the systemic and local administration of the compounds of the present invention and comparative compounds.

In the evaluation of systemic administration, a test compound suspended into 1% gum arabic was subcutaneously injected into back of rats at doses of 0.01, 0.03, 0.1, and 0.3 mg/kg (5 ml/kg). After 60 minutes following the administration, 1% carrageenin (0.1 ml) was injecte into the plantar surface of the right hind paw. The paw volume was measured with a plethysmometer before and 3 hours after the carrageenin injection. The value was compared with the corresponding value of the control group, thus obtaining the edema inhibition rate, from which $ED_{40}$ was determined.

For the local administration test, the test compound suspended in 1% carrageenin was subcutaneously injected into a paw in the rats at doses of 0.01, 0.03, and 1.0 μg/paw (0.1 ml/paw). Three hours after the carrageenin injection, the volume of the edema was compared with the corresponding value of the control group, thus obtaining the edema inhibition rate, from which $ED_{40}$ was determined.

The ratio of the $ED_{40}$ values thus obtained was taken for the evaluation of the local selectivity.

$$\text{Local Selectivity} = \frac{(A)\ [ED_{40}\ \text{for Systemic Administration}]}{(B)\ [ED_{40}\ \text{for Local Administration}]}$$

The higher the value, the greater is the selectivity. The results are shown in Table 1.

TABLE 1

| | $ED_{40}$ values | | Local Selectivity (A)/(B) |
|---|---|---|---|
| | (A) Systemic Administration (mg/kg) | (B) Local Administration (μg/kg) | |
| Compound No. 1 of this invention | 0.28 | 0.08 | 3.50 |
| Compound No. 4 of this invention | 0.83 | 0.21 | 3.95 |
| dexamethasone-17-butylate | 0.18 | 0.29 | 0.62 |
| dexamethasone-17,21-dibutylate | 0.34 | 0.17 | 2.00 |

EXPERIMENTAL EXAMPLE 2

Skin Vessel Constriction Activity (Local Anti-inflammatory Effect on Human Skin)

Skin vessel constriction effects on human skin of the present invention were investigated according to the following method. Dexamethasone 17,21-dipropionate which is known as a very strong anti-inflammatory agent for external application was used as a comparative compound.

Fifteen (15) healthy male subjects who were free from any skin disease anamnesis, such as eczema, dermatosis, or the like, received the test. Test compounds were diluted with 95% ethanol to make 6 sample solutions with different concentrations; highest concentration: $1 \times 10^{-2}$, lowest concentration: $1 \times 10^{-7}$. A strap to which acryl cells (diameter: 12 mm, thickness: 2 mm, height, 3 mm) were fixed was applied to the back of each subject. The test compound solution was then dropped with a pippet, 0.02 ml per drop, according to a key-code allocated at random. After drying by air, the strap was peeled off. The coated area was covered with a polyvinylidene chloride film, of which the periphery was fixed with a strap for the patch test. The period of time during which the covering was applied was 16 hours. The judgment was made according to the following standard four times at 1, 2, 5, and 8 hours after the removal of the film.

Evaluation Standard

++: The coated skin was strongly pale.
+: The coated skin was distinctly pale.
±: The coated skin was slightly pale.
−: No change was observed in the coated skin.

The results were analyzed by the probit method to obtain the $ED_{50}$ value ($\geq$ +) at which the coated area was clearly pale. The results are shown in Table 2, in which the relative value for the compounds of the present invention determined by taking the $ED_{50}$ value for dexamethasone 17,21-dipropionate as 100 are given in parentheses.

TABLE 2

| | $ED_{50}$ value ($\geq$ +) concentration (%) | | | |
|---|---|---|---|---|
| | 1 hour | 2 hours | 5 hours | 8 hours |
| Compound No. 1 of this invention | $1.45 \times 10^{-4}$ (378) | $1.19 \times 10^{-4}$ (345) | $7.29 \times 10^{-4}$ (1182) | $1.24 \times 10^{-2}$ (257) |
| Compound No. 4 | $5.10 \times 10^{-4}$ | $3.17 \times 10^{-4}$ | $2.00 \times 10^{-3}$ | $1.36 \times 10^{-2}$ |

TABLE 2-continued

| | \multicolumn{4}{c}{$ED_{50}$ value ($\geq +$) concentration (%)} |
| | 1 hour | 2 hours | 5 hours | 8 hours |
|---|---|---|---|---|
| of this invention | (107) | (130) | (431) | (235) |
| dexamethasone-17,21-dipropionate | $5.48 \times 10^{-4}$ | $4.11 \times 10^{-4}$ | $8.62 \times 10^{-3}$ | $3.19 \times 10^{-2}$ |

The above experimental data show that the steroid derivatives of the present invention have strong anti-inflammatory activity, with higher the local selectivity than conventional compounds. Since the compounds of the present invention are strongly effective at the local area and exhibit weak systemic activity (side effect), they are very useful as a medicine for curing or alleviating inflammation or rheumatism in mammals including human being, especially as an anti-inflammatory steroid agent.

Compound (I) of the present invention can exhibit its effect by administration either orally or otherwise. Because of its excellent local selectivity, however, non-oral administration, e.g. through the skin, rectam, or the like, is preferable. Conventional base materials can be blended with Compound (I) for preparing external application preparations such as ointments, creams, lotions, cataplasms, and the like, or suppositories. Such base materials may include various kinds of oils and fats derived from plant or animals, water-soluble base materials, e.g. polyalkylene glycol; humectants, e.g. glycerol, propylne glycol; surface active agents, preservatives, stabilizers, pH adjusting agents, and the like.

SYNTHESIS EXAMPLE 1

Synthesis of dexamethasone 17α-cyclopropanecarboxylate
[9α-fluoro-11β,17,21-trihydroxy-16α-methylpregna-1,4-diene-3,20-dione 17-cyclopropanecarboxylate] (Compound 1)

2.36 g (6.01 mmol) of dexamethasone, 1.50 g (10.3 mmol) of trimethyl orthocyclopropanecarboxylate, and 30 mg of p-toluenesulfonic acid were dissolved into 6 ml of dimethylformamide, and the solution was stirred for 8 hours at 80° C. After cooling and an addition of 0.05 ml of pyridine, the reaction mixture was poured into ice water and extracted with chloroform. The extract was washed with water and dried over anhydrous sodium sulfate. After evaporating chloroform under reduced pressure, 60 ml of methanol, 20 ml of chloroform, and 1 ml of 2N aqueous solution of oxalic acid were added to the residue. The mixture was stirred for 7 hours at room temperature. After the reaction, the solvent was evaporated under reduced pressure and the residue was purified over silica gel column chromatography to obtain 1.56 g (yield: 56.4%) of the title compound as colorless crystals.

SYNTHESIS EXAMPLE 2

Synthesis of 21-desoxydexamethasone 17α-cyclocarboxylate
[9α-fluoro-11β,17-dihydroxy-16α-methylpregna-1,4-diene-3,20-dione 17-cyclopropanecarboxylate] (Compound 2)

0.92 g (2.00 mmol) of dexamethasone 17α-cyclopropanecarboxylate was dissolved into 20 ml of anhydrous tetrahydrofuran. After an addition of 1.0 ml (7.18 mmol) of triethylamine, 0.30 ml (3.87 mmol) of methanesulfonyl chloride was added dropwise, followed by stirring for 8 hours at room temperature. The solvent was evaporated under reduced pressure and the residue was dissolved into chloroform, washed with water, and dried over anhydrous sodium sulfate. After evaporating chloroform under reduced pressure, the residue was crystallized from ether to obtain 0.864 g (yield: 80%) of dexamethasone 17α-cyclopropanecarboxylate 21-methanesulfonate as colorless crystals.

0.101 g (0.189 mmol) of the methanesulfonate was dissolved into 5 ml of dimethylformamide and 100 mg (0.667 mmol) of sodium iodide was added to the solution. After refluxing for 30 minutes, dimethylformamide was evaporated under reduced pressure. To the residue was added 30 ml of a 5% aqueous solution of sodiun methabisulfite and the mixture was stirred for 30 minutes at room temperature. The reaction mixture was extracted with chloroform, washed with water, and dried over anhydrous sodium sulfate. After evaporating chloroform under reduced pressure, the residue was purified over silica gel column chromatography to obtain 53 mg (yield: 63%) of the title compound as colorless crystals.

SYNTHESIS EXAMPLE 3

Synthesis of dexamethasone 21-chloride 17α-cyclopropanecarboxylate
[21-chloro-9α-fluoro-11β,17-dihydroxy-16α-methyl-pregna-1,4-diene-3,20-dione 17-cyclopropanecarboxylate] (Compound 3)

171 mg (0.32 mmol) of dexamethasone 17α-cyclopropanecarboxylate 21-methansulfonate was dissolved into 10 ml of dimethylformamide. After an addition of 200 mg (9.09 mmol) of lithium chloride, the mixture was stirred for 7 hours at 120° C. Dimethylformamide was evaporated under reduced pressure and the residue was dissolved into chloroform, washed with water, and dried over anhydrous sodium sulfate. After evaporating chloroform under reduced pressure, the residue was purified over silica gel column chromatography to obtain 0.105 g (yield: 69.2%) of the title compound as colorless crystals.

SYNTHESIS EXAMPLE 4

Synthesis of dexamethasone 17α,21-dicyclopropanecarboxylate
[9α-fluoro-11β,17,21-trihydroxy-16α-methylpregna-1,4-diene-3,20-dione 17,21-dicyclopropanecarboxylate] (Compound 4)

1.04 g (2.26 mmol) of dexamethasone 17α-cyclopropanecarboxylate was dissolved into 20 g of anhydrous tetrahydrofuran. After an addition of 1.0 ml (7.18 mmol) of triethylamine, 0.50 g (4.78 mmol) of cyclopropanecarbonyl chloride was added dropwise, followed by stirring for 8 hours at room temperature. The solvent was evaporated under reduced pressure and the residue was dissolved into chloroform, washed with water, and dried over anhydrous sodium sulfate. After evaporating chloroform under reduced pressure, the residue was purified over silica gel column chromatography to obtain 0.96 g (yield: 80.7%) of the title compound as colorless crystals.

SYNTHESIS EXAMPLES 5-16

Compounds 5-16 were prepared in the same manner as Synthesis Examples 1-4.

Analysis and characteristics of Compounds 1-16 are given in Table 3.

TABLE 3

| Comd. No. | R in equation (I) | $^{13}$C-NMR δ ppm (CDCl$_3$) | $^1$H-NMR δ ppm (CDCl$_3$) | IR$_{max}^{KBr}$ cm$^{-1}$ | Specification (mp: °C.) |
|---|---|---|---|---|---|
| 1 | OH | 8.6, 9.2, 12.7, 16.4, 16.7, 22.9(× ½), 23.1 (× ½), 27.4, 31.0, 33.6(× ½), 33.9, 34.5(× ½), 35.2, 36.4, 43.5, 47.8 (× ½), 48.4, 48.9(× ½), 67.1, 70.8 (× ½), 72.5(× ½), 94.3, 96.5(× ½), 104.3(× ½), 125.0, 129.6, 152.7, 166.7, 174.6, 186.8, 205.1 | 0.40-3.70(m, 18H), 0.94(d, 3H), 1.02(s, 3H), 1.56(s, 3H), 4.25(s, 2H), 4.40(m, 1H), 6.16(br, 1H), 6.34(dd, 1H), 7.34(d, 1H) | 3400, 1720, 1660, 1615, 1600 | Colorless Crystal 226-227 |
| 2 | H | 8.4, 8.9, 12.8, 16.5(× 2), 22.9(× ½), 23.1(× ½), 27.4(× 2), 31.1, 33.6, 33.6(× ½), 34.5(× ½), 34.7, 37.0, 43.7, 47.5, 48.0(× ½), 48.9(× ½), 70.8 (× ½), 72.5(× ½), 96.6(× ½), 97.2, 104.4(× ½), 124.8, 129.5, 152.9, 167.1, 174.3, 186.8, 202.9 | 0.40-2.80(m, 15H), 0.88 (d, 3H), 1.00(s, 3H), 1.56 (s, 3H), 2.00(s, 3H), 3.40 (m, 1H), 3.74(br, 1H), 4.40 (m, 1H), 6.16(br, 1H), 6.36 (dd, 1H), 7.38(d, 1H) | 3400, 1710, 1660, 1605 | Colorless Crystal 210-212 |
| 3 | Cl | 8.9, 9.4, 12.7, 16.5, 16.7, 22.9(× ½), 23.1(× ½), 27.5, 31.2, 33.6, 33.8(× ½) 34.7(× ½), 35.8, 36.4, 43.8(× ½), 43.9 (× ½), 45.6, 48.2(× ½), 48.4, 49.1 (× ½), 70.6(× ½), 72.2(× ½), 96.8, 96.8(× ½), 104.5(× ½), 124.8, 129.5, 153.4, 167.7, 175.2, 187.4, 197.6 | 0.70-3.00(m, 16H), 0.92 (d, 3H), 1.06(s, 3H), 1.56 (s, 3H), 3.36(m, 1H), 4.04 (s, 2H), 4.44(m, 1H), 6.20 (br, 1H), 6.40(dd, 1H), 7.32(d, 1H) | 3390, 1725, 1660, 1600 | Colorless Crystal 251-252 |
| 4 | OCO—△ | 8.6, 8.9(× 2), 9.2, 12.7(× 2), 16.2, 16.7, 22.9(× ½), 23.1(× ½), 27.4, 31.0, 33.6 (× ½), 33.9, 34.5(× ½), 35.4, 36.6, 43.5, 47.7(× ½), 48.3, 48.8(× ½), 67.0, 70.9(× ½), 72.6(× ½), 95.0, 96.4 (× ½), 104.2(× ½), 125.1, 129.7, 152.3, 166.2, 174.5(× 2), 186.5, 198.1 | 0.20-3.40(m, 22H), 0.96 (d, 3H), 1.08(s, 3H), 1.56 (s, 3H), 4.40(m, 1H), 4.80 (s, 2H), 6.20(br, 1H), 6.40, (dd, 1H), 7.36(d, 1H) | 3500, 1730, 1660, 1620, 1605 | Colorless Crystal 240-241 |
| 5 | OCO—◇ | 8.6, 9.2, 12.7, 16.3, 16.7, 18.5, 22.9 (× ½), 23.2(× ½), 25.3(× 2), 27.4, 31.0, 33.6(× ½), 33.9, 34.5(× ½), 35.4 36.7, 37.9, 43.5, 47.8(× ½), 48.4, 48.8 (× ½), 66.9, 71.0(× ½), 72.7(× ½), 95.1, 96.4(× ½), 104.2(× ½), 125.1, 129.8, 152.4, 166.3, 174.5, 175.1, 186.6, 198.0 | 0.60-3.40(m, 24H), 0.94(d, 3H), 1.10(s, 3H), 1.56(s, 3H), 4.40(m, 1H), 4.80(s, 2H), 6.18(br, 1H), 6.38(dd, 1H), 7.34(d, 1H) | 3500, 1730, 1660, 1620, 1605 | Colorless Crystal 237-238 |
| 6 | OCO—⬠ | 8.6, 9.2, 12.7, 16.2, 16.7, 22.9(× ½), 23.1(× ½), 25.8(× 2), 27.4, 30.0, 30.1, 31.0, 33.6(× ½), 33.9, 34.5(× ½), 35.4 36.7, 43.5(× 2), 47.8(× ½), 48.3, 48.8 (× ½), 66.8, 70.9(× ½), 72.6(× ½), 95.1, 96.4(× ½), 104.2(× ½), 125.0, 129.7, 152.4, 166.3, 174.5, 176.4, 186.6, 198.0 | 0.70-3.40(m, 26H), 0.96 (d, 3H), 1.10(s, 3H), 1.54 (s, 3H), 4.40(m, 1H), 4.82 (s, 2H), 6.18(br, 1H), 6.40 (dd, 1H), 7.32(d, 1H) | 3500, 1725, 1660, 1615, 1605 | Colorless Crystal 206-207 |
| 7 | OCO—⬡ | 8.6, 9.2, 12.7, 16.2, 16.7, 22.9(× ½), 23.1(× ½), 25.4(× 2), 25.7, 27.4, 29.0 (× 2), 31.0, 33.6(× ½), 33.9, 34.5 (× ½), 35.4, 36.7, 42.9, 43.5, 47.8 (× ½), 48.3, 48.8(× ½), 66.6, 70.9 (× ½), 72.6(× ½), 95.1, 96.4(× ½) 104.2(× ½), 125.1, 129.8, 152.3, 166.2, 174.5, 175.7, 186.5, 198.0 | 0.60-3.40(m, 28H), 0.96 (d, 3H), 1.08(s, 3H), 1.56 (s, 3H), 4.40(m, 1H), 4.76 (s, 2H), 6.16(br, 1H), 6.36 (dd, 1H), 7.32 (d, 1H) | 3300, 1730, 1660, 1605 | Colorless Crystal 267-268 |
| 8 | OCOCH$_3$ | 8.6, 9.2, 12.7, 16.2, 16.7, 20.6, 22.9 (× ½), 23.1(× ½), 27.4, 31.0, 33.6 (× ½), 33.9, 34.5(× ½), 35.4, 36.6, 43.5, 47.8(× ½), 48.4, 48.8(× ½), 67.1, 70.9(× ½), 72.5(× ½), 95.0, 96.4 (× ½), 104.2(× ½), 125.0, 129.7, 152.4, 166.3, 170.6, 174.6, 186.6, 198.1 | 0.60-3.40(m, 17H), 0.94(d, 3H), 1.08(s, 3H), 1.56(s, 3H), 2.16(s, 3H), 4.40(m, 1H), 4.80(s, 2H), 6.18(br, 1H), 6.38(dd, 1H), 7.34(d, 1H) | 3475, 1750, 1720, 1660, 1615, 1605 | Colorless Crystal 245-246 |
| 9 | OCOCH$_2$CH$_3$ | 8.7, 9.1, 9.3, 12.7, 16.3, 16.7, 22.9 (× ½), 23.2(× ½), 27.3, 27.4, 31.0, 33.6(× ½), 33.9, 34.5(× ½), 35.4, 36.7, 43.5, 47.8(× ½), 48.4, 48.8(× ½), 67.0, 71.0(× ½), 72.7(× ½), 95.0, 96.4 (× ½), 104.2(× ½), 125.1, 129.8, 152.4, 166.3, 174.1, 174.6, 186.6, 198.1 | 0.40-3.40(m, 17H), 0.94(d, 3H), 1.10(s, 3H), 1.18(t, 3H), 1.56(s, 3H), 2.48(q, 2H), 4.40(m, 1H), 4.80(s, 2H), 6.18(br, 1H), 6.40(dd, 1H), 7.34(d, 1H) | 3480, 1730, 1660, 1620, 1605 | Colorless Crystal 242-243 |
| 10 | OCO(CH$_2$)$_8$CH$_3$ | 8.6, 9.2, 12.7, 14.0, 16.2, 16.7, 22.6, 22.9 (× ½), 23.1(× ½), 24.9, 27.4, 29.1, | 0.70-3.50(m, 36H), 0.94(d, 3H), 1.08(s, 3H), | 3450, 2920, 1720, 1660 | Colorless Waxy |

TABLE 3-continued

| Comd. No. | R in equation (I) | $^{13}$C-NMR δ ppm (CDCl$_3$) | $^1$H-NMR δ ppm (CDCl$_3$) | IR$_{max}^{KBr}$ cm$^{-1}$ | Specification (mp: °C.) |
|---|---|---|---|---|---|
| | | 29.2(× 2), 29.4, 31.0, 31.9, 33.6(× ½), 33.9(× 2), 34.5(× ½), 35.4, 36.7, 43.5, 47.8(× ½), 48.3, 48.8(× ½), 66.9, 71.0 (× ½), 72.7(× ½), 95.0, 96.3(× ½), 104.1(× ½), 125.1, 129.7, 152.4, 166.3, 173.4, 174.5, 186.6, 198.0 | 1.56(s, 3H), 4.40(m, 1H), 4.78(s, 2H), 6.16(br, 1H), 6.36(dd, 1H), 7.30(d, 1H), | 1620 | Substance |
| 11 | OCO(CH$_2$)$_{14}$CH$_3$ | 8.6, 9.2, 12.7, 14.0, 16.2, 16.7, 22.6 (× ½), 22.8(× ½), 24.9, 27.3, 29.3 (× 2), 29.5(× 2), 29.6(× 7), 31.0, 31.9, 33.6(× ½), 33.9(× 2), 34.5(× ½), 35.4, 36.7, 43.4, 47.7(× ½), 48.3, 48.7(× ½) 66.9, 71.0(× ½), 72.7(× ½), 94.9, 96.3 (× ½), 104.1(× ½), 125.1, 129.8, 152.0, 166.0, 173.5, 174.5, 186.5, 198.0 | 0.20–3.40(m, 48H), 0.96(d, 3H), 1.08(s, 3H), 1.56(s, 3H), 4.40(m, 1H), 4.80(s, 2H), 6.18 (br, 1H), 6.38(dd, 1H), 7.30(d, 1H) | Neat 3450, 2930, 1720, 1660, 1620 | Colorless Oily Substance |
| 12 | 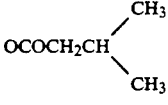 OCOCH$_2$CH(CH$_3$)$_2$ | 8.6, 9.2, 12.7, 16.2, 16.7, 22.4(× 2), 22.9 (× ½), 23.1(× ½), 25.6, 27.4, 31.0, 33.6(× ½), 33.9, 34.5(× ½), 35.4, 36.7, 43.0, 43.5, 47.7(× ½), 48.3, 48.8(× ½), 66.8, 71.0(× ½), 72.7(× ½), 95.0, 96.3 (× ½), 104.1(× ½), 125.1, 129.8, 152.2, 166.1, 172.6, 174.5, 186.5, 197.9 | 0.60–3.60(m, 20H), 0.98(d, 9H), 1.09(s, 3H), 1.56(s, 3H), 4.40(m, 1H), 4.80(s, 2H), 6.18(br, 1H), 6.38(dd, 1H), 7.34(d, 1H) | 3500, 1730, 1660, 1620 | Colorless Crystal 207–208 |
| 13 | OCOC(CH$_3$)$_3$ | 8.6, 9.2, 12.8, 16.2, 16.8, 22.9(× ½), 23.2(× ½), 27.3(× 4), 31.0, 33.6(× ½) 33.9, 34.5(× ½), 35.5, 36.7, 38.8, 43.5, 47.8(× ½), 48.4, 48.8(× ½), 66.9, 71.0 (× ½), 72.7(× ½), 95.2, 96.4(× ½), 104.2(× ½), 125.1, 129.8, 152.3, 166.3, 174.5, 178.3, 186.6, 197.8 | 0.60–3.40(m, 17H), 0.94(d, 3H), 1.10(s, 3H), 1.26(s, 9H), 1.56(s, 3H), 4.40(m, 1H), 4.80(s, 2H), 6.18(br, 1H), 6.38(dd, 1H), 7.34(d, 1H) | 3500, 1720, 1650, 1615, 1600 | Colorless Crystal 235–236 |
| 14 | OCO(CH$_2$)$_3$—Cl | 8.7, 9.3, 12.7, 16.3, 16.7, 22.9(× ½), 23.2(× ½), 27.4, 27.8, 31.0(× 2), 33.6 (× ½), 33.9, 34.5(× ½), 35.4, 36.7, 43.5, 43.9, 47.8(× ½), 48.4, 48.8(× ½), 67.1, 71.0(× ½), 72.7(× ½), 95.0, 96.4 (× ½), 104.2(× ½), 125.1, 129.8, 152.3, 166.2, 172.2, 174.6, 186.6, 197.9 | 0.60–3.40(m, 21H), 0.96(d, 3H), 1.10(s, 3H), 1.56(s, 3H), 3.64(t, 2H), 4.44(m, 1H), 4.82(s, 2H), 6.20(br, 1H), 6.40(dd, 1H), 7.36(d, 1H) | 3370, 1760, 1725, 1660, 1610 | Colorless Crystal 197–198 |
| 15 | 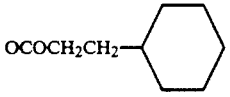 OCOCH$_2$CH$_2$-cyclohexyl | 8.6, 9.2, 12.7, 16.3, 16.7, 22.9(× ½), 23.1(× ½), 26.2(× 2), 26.5, 27.4, 31.0, 31.5, 32.2, 33.0(× 2), 33.6(× ½), 33.9, 34.5(× ½), 35.4, 36.8, 37.2, 43.4, 47.7 (× ½), 48.3, 48.7(× ½), 67.0, 71.0 (× ½), 72.8(× ½), 94.9, 96.4(× ½), 104.2(× ½), 125.2, 129.8, 151.9, 165.8, 173.8, 174.5, 186.4, 197.9, | 0.60–3.80(m, 32H), 0.96(d, 3H), 1.08(s, 3H), 1.56(s, 3H), 4.40(m, 1H), 4.80(s, 2H), 6.20(br, 1H), 6.40(dd, 1H), 7.32(d, 1H) | 3300, 1720, 1660, 1600 | Colorless Crystal 186–187 |
| 16 | 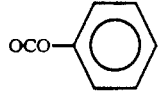 OCO-phenyl | 8.3, 9.3, 12.8, 16.2, 16.8, 22.9(× ½), 23.1(× ½), 27.5, 31.1, 33.7(× ½), 33.9, 34.6(× ½), 35.6, 36.4, 43.7, 48.0(× ½), 48.6, 49.0(× ½), 67.7, 70.8(× ½), 72.4 (× ½), 95.5, 96.7(× ½), 104.5(× ½), 124.9, 128.5(× 2), 129.4, 129.5, 130.0 (× 2), 133.5, 153.1, 166.6, 167.1, 174.8, 187.1, 198.0 | 0.40–3.50(m, 17H), 0.96(d, 3H), 1.12(s, 3H), 1.56(s, 3H), 4.36(m, 1H), 4.94(d, 1H), 5.16(d, 1H), 6.18(br, 1H), 6.38(dd, 1H), 7.36(d, 1H), 7.60(m, 3H), 8.18(m, 2H) | 3400, 1720, 1660, 1620, 1610 | Colorless Crystal 259–260 |

PREPARATION EXAMPLE 1

| | (gram) |
|---|---|
| Compound 1 | 0.05 |
| White petrolatum | 89.95 |
| Light liquid paraffin | 5 |
| Propylene glycol | 5 |
| | 100 |

An ointment having the above formulation was prepared according to a conventional method.

PREPARATION EXAMPLE 2

| | (gram) |
|---|---|
| Compound 4 | 0.05 |
| Cetanol | 5 |
| White petrolatum | 7 |
| Isopropyl myristate | 5 |
| Glycerol monostearate | 4 |
| Polyoxyethylenecetyl ether (20EO) | 2.5 |
| Methyl paraoxybenzoate | 0.1 |
| Propyl paraoxybenzoate | 0.05 |
| Purified water | 76.3 |
| | 100 |

A cream was prepared using the above formulation according to a conventional method.

Obviously, numerous modifications and variations of the present invention are possible in light of the above teachings. It is therefore to be understood that within the scope of the appended claims, the invention may be practiced otherwise than as specifically described herein.

What is claimed is:

1. A steroid derivative represented by formula (I),

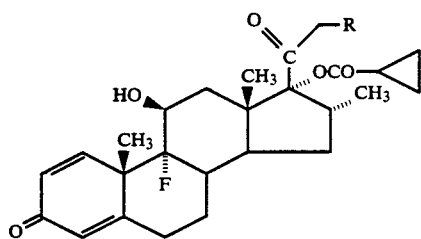

wherein R is a hydrogen atom, a halogen atom, a hydroxy group, or a group —OCOR₁, wherein R₁ is a linear or branched alkyl group which may be substituted by a halogen atom or a cycloalkyl group, a cycloalkyl group, or an aryl group.

2. A pharmaceutical composition for treating inflammation or rheumatism, comprising: as an active component, a pharmaceutically effective amount of a steroid derivative represented by formula (I),

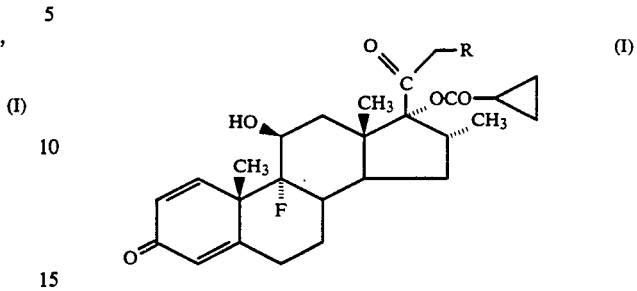

wherein R is a hydrogen atom, a halogen atom, a hydroxy group, or a group—OCOR₁, wherein R₁ is a linear or branched alkyl group which may be substituted by a halogen atom or a cycloalkyl group; a cycloalkyl group, or an aryl group in combination with a pharmaceutically acceptable carrier.

* * * * *